US006814729B2

(12) United States Patent
Youssefi et al.

(10) Patent No.: US 6,814,729 B2
(45) Date of Patent: Nov. 9, 2004

(54) LASER VISION CORRECTION APPARATUS AND CONTROL METHOD

(75) Inventors: Gerhard Youssefi, Landshut (DE); Kristian Hohla, Vaterstetten (DE); Stefan Lang, Markt Schwaben (DE)

(73) Assignee: TechnoVision GmbH, Munich (DE)

( * ) Notice: Subject to any disclaimer, the term of this patent is extended or adjusted under 35 U.S.C. 154(b) by 83 days.

(21) Appl. No.: 10/184,441

(22) Filed: Jun. 27, 2002

(65) Prior Publication Data

US 2004/0002695 A1 Jan. 1, 2004

(51) Int. Cl.[7] .............................................. A61B 9/007
(52) U.S. Cl. ............................................ 606/10; 606/5
(58) Field of Search ................................. 606/5, 10–13

(56) References Cited

U.S. PATENT DOCUMENTS

| 4,669,466 A | * | 6/1987 | L'Esperance | 606/10 |
|---|---|---|---|---|
| 5,683,379 A | | 11/1997 | Hohla | 606/5 |
| 5,827,264 A | | 10/1998 | Hohla | 606/5 |
| 5,891,132 A | | 4/1999 | Hohla | 606/5 |
| 6,090,100 A | | 7/2000 | Hohla | 606/5 |
| 6,106,513 A | * | 8/2000 | McMillen et al. | 606/10 |
| 6,139,542 A | | 10/2000 | Hohla | 606/5 |
| 6,296,634 B1 | | 10/2001 | Munnerlyn et al. | 606/10 |
| 6,299,309 B1 | | 10/2001 | Ruiz | 351/212 |
| 6,364,873 B1 | | 4/2002 | McMillen | 606/10 |
| 2003/0073984 A1 | | 4/2003 | Maeda | 606/5 |

FOREIGN PATENT DOCUMENTS

EP 0 280 414 A1 1/1998
EP 1 044 755 A2 3/2000

OTHER PUBLICATIONS

US Pub. No. 2002/0091376A1 Entitled "Ophthalmological Surgery Technique with Active Patient Data Card" by McMillen, published Jul. 11, 2002.

Knorz, et al., "Treatment of Myopia and Myopic Astigmatism by Customized Laser In Situ Keratomileusis Based on Corneal Topography," *American Academy of Ophthalmology*, vol. 107, No. 11, Nov. 2000, pp. 2072–2076.

Mrochen, et al., "Wavefront–Guided Laser In Situ Keratomileusis: Early Results in Three Eyes," *Journal of Refractive Surgery*, vol. 16, No. 2, Mar./Apr. 2000, pp. 116–121.

Knorz et al., "Topographically–Guided Laser In Situ Keratomileusis to Treat Corneal Irregularities," *American Academy of Ophthalmology*, vol. 107, No. 6, Jun. 2000, pp. 1138–1143.

* cited by examiner

Primary Examiner—David M. Shay

(57) ABSTRACT

A device readable medium for use in controlling a laser vision correction system includes a storage structure having stored therein a pre-programmed first, readable, corrective instruction reference that corresponds to an encoded customized corrective instruction determined by a calculation module external to the medium. The encoded customized corrective instruction is executable by a laser vision correction laser platform for correction of a refractive defect when the corrective instruction reference is properly recognized. A laser vision correction system including the device readable medium is described. A remunerative model relating to the device readable medium is disclosed.

47 Claims, 6 Drawing Sheets

LASER VISION CORRECTION APPARATUS AND CONTROL METHOD

BACKGROUND OF THE INVENTION

1. Field of the Invention

The invention is generally directed to the field of laser vision correction, and more particularly, to laser vision correction systems and control apparatus and methods.

2. Description of Related Art

Ultraviolet laser systems and related methods are known for enabling ophthalmic surgery on the cornea in order to correct vision defects. Techniques for ablative photodecomposition include, but are not limited to, LASIK, LASEK, and PRK. Conventional treatment by these techniques is typically indicated for refractive defects including myopia, hyperopia, and presbyopia, with or without astigmatism. In some cases, re-treatment from a previous surgery is also indicated.

Although surgeons administer the ophthalmic treatment, it is typically the laser manufacturers who program their lasers with tissue ablation algorithms to effect suitable treatment for the various diagnosed refractive defects. As used herein, the term "tissue ablation algorithm" refers to the process or procedure carried out in and by the hardware/software of the laser system. As illustrated schematically by the laser system 10 in FIG. 1, some type of diagnostic input 12 from a surgeon and/or one or more diagnostic devices 14 is sent to a laser platform 16. The laser platform includes a computer-linked control system 18 that utilizes software to compute an appropriate laser ablation shot file based upon optical zone size and other input parameters entered by the surgeon. The laser platform also includes hardware in the form of beam shaping and steering optics that react to instructions from the control system to deliver the shot file in the appropriate manner to the cornea. Thus, the laser platform is a "smart" device, so to speak, because it is there that both information processing and treatment execution occur. In an aspect shown by the dotted lines, the laser platform is capable of receiving a computer-readable medium 20 having both enablement and instructional software stored therein which can be processed by the computer system in the laser platform.

Certain disadvantages attach to the methodologies such as those described above. In the first case described, the laser platform is burdened with computer hardware and software adding to the complexity and cost of every unit. In the second scenario described above, the computer-readable medium may be in the form of a single use enablement card, for example, as described in U.S. Pat. Nos. 6,296,634 and 6,364,873. Such enablement cards are typically purchased by a user, and generate a set per-procedure fee for the laser manufacturer. Each treatment procedure requires a card, while the laser system continues to require the necessary computer hardware and software as mentioned above. Thus the laser system lacks flexibility and is no less burdened than described above. Moreover, there are many aspects of the laser platform that can malfunction, increasing the risk of surgical downtime for the user. Trained technicians having skills in multiple technical fields are required to maintain and service the multi-component laser platforms.

In view of the foregoing and other disadvantages currently associated with typical laser vision correction systems, the inventors have recognized a need for improvements that increase the flexibility and reduce the cost of making, supplying, maintaining, and controlling laser vision correction systems, and which make it easier for the surgeon to provide the best treatment outcomes for their patients.

SUMMARY OF THE INVENTION

The invention is generally directed to apparatus and methods involved in the control of a laser vision correction system, and a system incorporating these controls.

An embodiment of the invention is directed to a device-readable medium on or in which is stored a pre-programmed, readable, first corrective instruction reference. This instruction reference corresponds to an encoded customized corrective instruction. As used herein, the term "customized corrective instruction" refers to the number, sequence, and placement of laser pulses for a particular laser vision correction treatment. The instruction is determined by a calculation module located external to the medium and to the laser platform, and is executable by the laser platform of a laser vision correction system. The customized corrective instruction is determined in a manner that will be described in greater detail below. A particular customized corrective instruction is then encoded in such a manner that the instruction can be executed by the laser platform upon recognition of the corresponding instruction reference stored in or on the medium. In an aspect of this embodiment, the first corrective instruction reference stored in or on the medium is a necessary and sufficient component for enabling the laser platform to execute the customized instruction when the instruction reference is properly recognized. In an alternative aspect, the first instruction reference is a necessary but not sufficient component for allowing enablement and execution of the customized instruction by the laser platform. Rather, a second, readable corrective instruction reference is stored in or on the medium and in combination with the first corrective instruction reference, is sufficient for enabling execution of the customized instruction. Preferably, the second instruction reference will correspond to an encoded user ID or laser platform ID which will be associated with the customized instruction. In an alternative aspect, the medium may have stored therein a second pre-programmed instruction reference and a third pre-programmed instruction reference, corresponding to a user ID and a laser platform ID, in addition to the first instruction reference corresponding to the customized corrective instruction. In this aspect, all three matching instruction references are necessary and, in combination, sufficient components for enabling the execution of the customized instruction by the laser platform. With respect to all of the aspects referred to above, the total data storage requirement for any or all of the instruction references in combination, along with any other information stored in the medium, preferably will not exceed 1000 bytes of storage space. In another aspect according to this embodiment, the medium includes a laser platform disablement feature that limits a preset number of uses of the laser platform for each readable medium unit. This feature provides an annuity structure for laser system use as is well known in the art. In a further aspect, the medium includes a beam sizing and shaping feature to provide a desired beam diameter and beam energy profile for ablating a corneal surface and/or facilitating beam diagnostics.

In another embodiment according to the invention, a laser vision correction system includes a calculation module that can receive input data relating at least to a refractive defect of a patient's eye and calculate a customized corrective instruction based, at least in part, upon the input data. As used herein, the term calculation module refers either to a hardware device, computer-executable software which per-forms all pertinent aspects of an ablation treatment algorithm, or a combination of hardware, software, and/or firmware for determining the customized corrective instruction. The calculated customized corrective instruction is then encoded such that the encryption will allow a matching correspondence to a pre-programmed first corrective instruction reference that is stored in or on a device-readable medium. The system further includes a laser platform that can receive the readable medium and execute the customized corrective instruction, as a necessary condition, only when the first corrective instruction reference corresponding to the encoded customized corrective instruction is recognized by the laser platform. The calculation module is external to the laser platform and preferably resides in a diagnostic platform that is used to generate at least some of the input data. In a preferred aspect of this embodiment, the customized corrective instruction calculated by the calculation module may include more than one particular corrective instruction for each of a variety of laser vision corrective treatments. For example, depending upon the input data, the calculation module may generate three different corrective instructions for myopia treatments, or, two different instructions for hyperopia treatments, that, when encoded, correspond to the first corrective instruction reference on the storage medium, thus potentially providing the user with a choice of appropriate treatment options. In a related aspect, the system includes a graphical user interface (GUI) that is operably associated with the laser platform, along with a configuration file that is also operably associated with the laser platform and the GUI. In this aspect, the configuration file will recognize the instruction reference corresponding to the customized corrective instruction and will then initiate a particular GUI associated with the one or more matched, customized corrective instructions. The GUI will then allow the user to input information that will result in the selection of a single matching instruction reference recognized by the configuration file in the laser platform that will enable and allow the laser platform to execute the particular customized refractive instruction.

In another embodiment, a method for controlling a laser vision correction system includes providing a device-readable medium having the attributes of the device-readable medium set forth hereinabove, for use in a laser platform to execute a particular laser vision correction procedure. It further includes providing the medium to a third party on a remunerative basis; and, structuring the remuneration as a function of type and/or number of corresponding instruction references supplied in the medium.

Another method embodiment for controlling a laser vision correction system involves determining a customized corrective instruction for correcting an ophthalmic refractive defect, encoding the instruction, providing a transferable device-readable medium that includes a pre-programmed, first corrective instruction reference which corresponds to the encoded instruction, and providing a laser platform that can receive the transferable medium and recognize the corresponding first instruction reference as a necessary condition for enabling execution of the customized corrective instruction. In a preferred aspect, the method further includes providing a GUI that is operably connected with the laser platform and which is configured according to the instruction reference corresponding to the encoded instruction. In a further related aspect, the method includes providing either or both of an encoded user ID and an encoded laser platform ID, and providing associated second and/or third corresponding instruction references in the transferable medium which are recognizable as necessary and, perhaps, sufficient conditions for allowing execution of the customized corrective instruction. In addition to, or in place of, the second and/or third instruction reference, other corresponding codes can be stored in the medium; e.g., iris pattern codes. The medium storage structure may further be writeable such that the medium could be inserted into a component of the diagnostic platform to directly receive specific encoded or uncoded data.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF A PREFERRED EMBODIMENT

Figure 1:
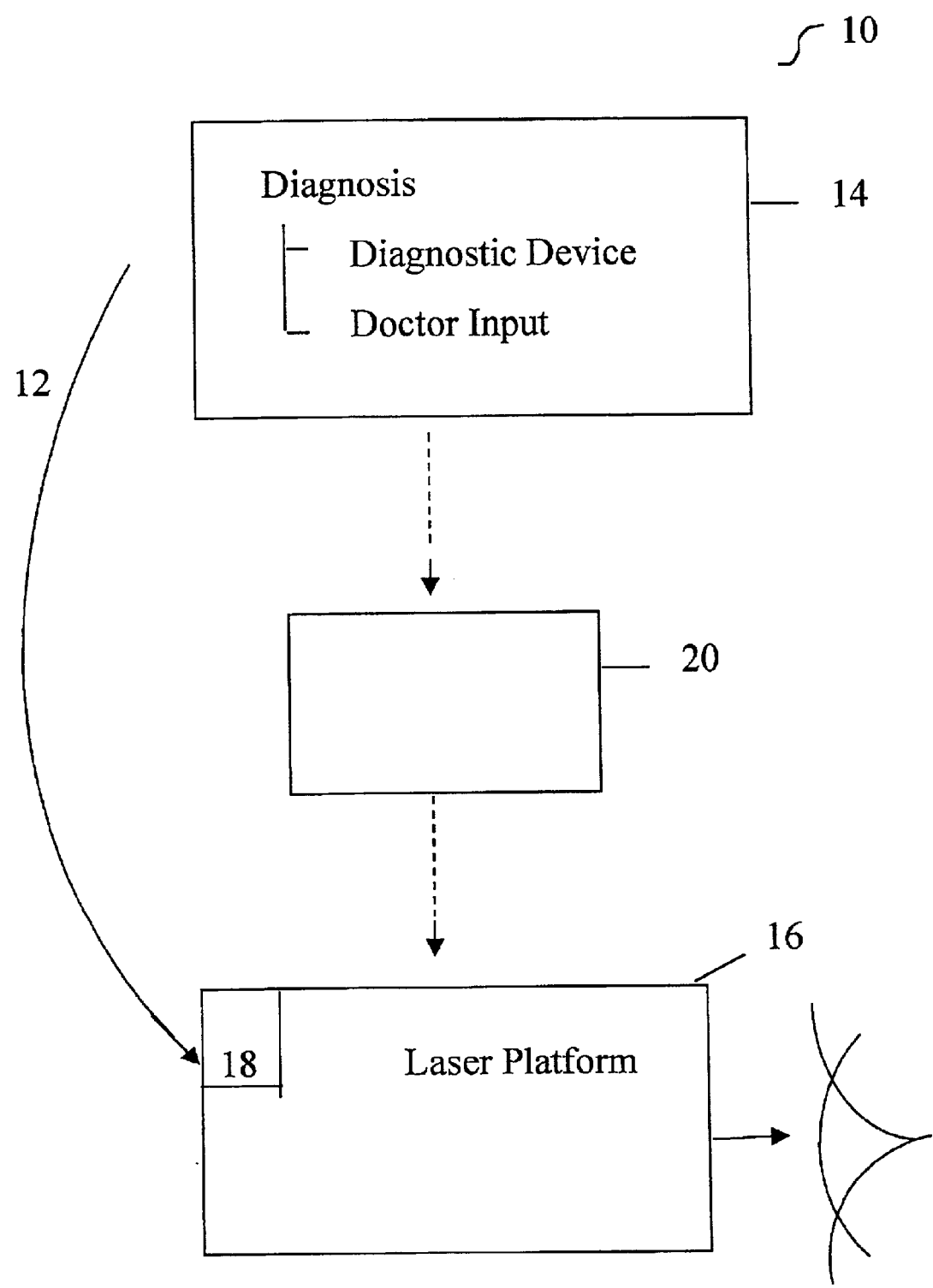
FIG. 1 is a block diagram of a prior art laser vision correction system.
Figure 2:
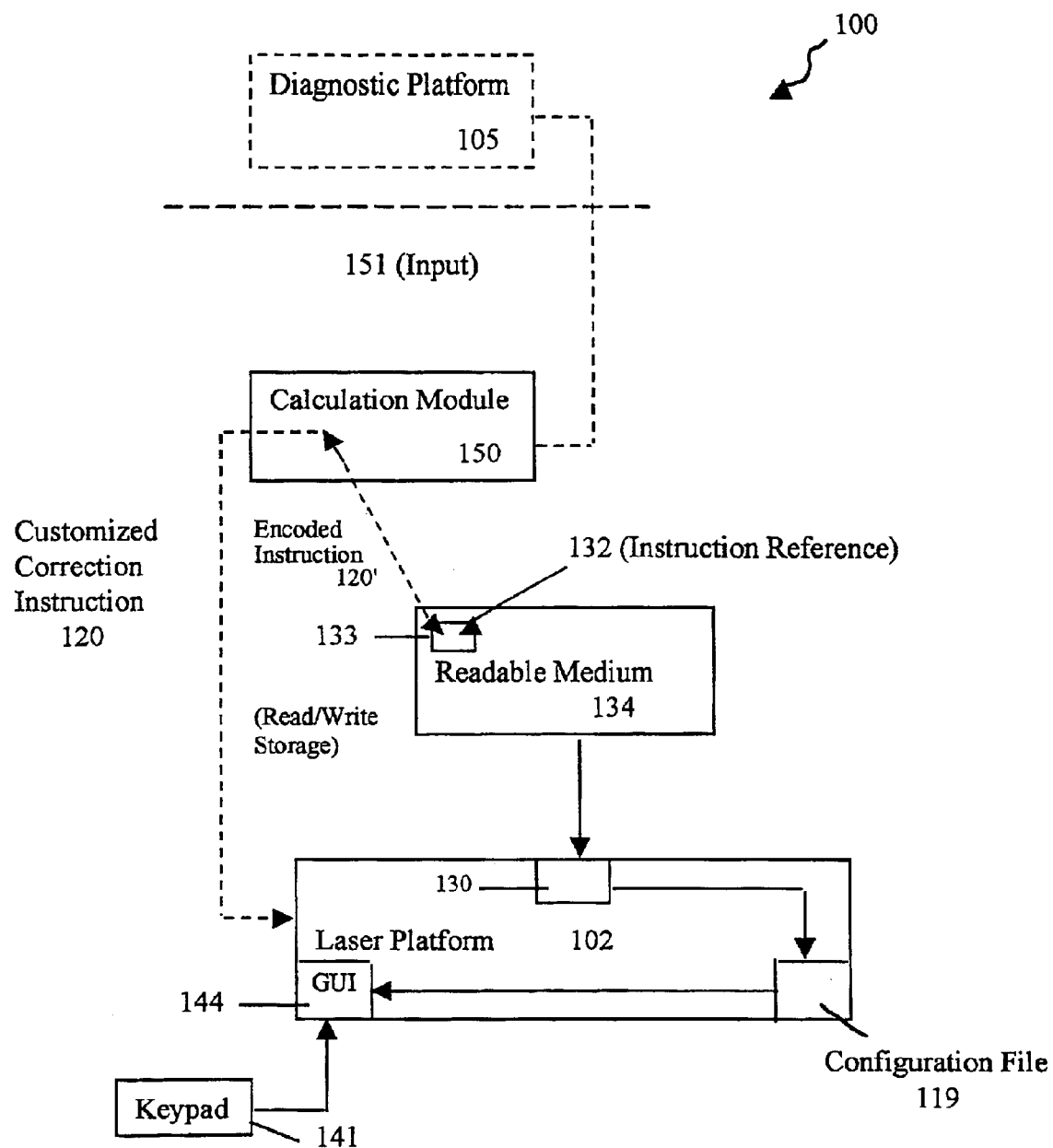
FIG. 2 is a block diagram of a laser vision correction system according to an embodiment of the invention.

FIG. 2 shows a simplified block diagram of a laser vision correction system 100 according to a preferred embodiment of the invention. The basic components of the system include a calculation module 150, a laser platform 102, and a device readable medium 134 that is transferable to and readable by the laser platform 102. The readable medium 134 is preferably in the form of a card similar in size and shape to a credit card. The card medium 134 includes a section 133 for storing data that can be read by an appropriate card reader 130 located in the laser platform 102.

The calculation module 150 receives input data 151 from what is referred to as a diagnostic platform 105. The diagnostic platform 105 can be comprised of a single diagnostic instrument that provides diagnostic information relating to a patient's refractive defect, or any combination of various diagnostic instruments and/or other forms of outcome influencing information that a surgeon may wish to enter. In a preferred embodiment, the calculation module 150 is an executable computer software routine that runs in a diagnostic wavefront sensing device 105. Wavefront measurement information is fed into the calculation module 150 which then uses that information to calculate one or more appropriate laser treatments. These treatments are referred to herein as customized corrective instructions 120. These instructions ultimately instruct a fire control system (not shown) in the laser platform 102 where to direct a series of laser pulses on the patient's cornea to effect the appropriate laser vision correction treatment.

Figure 4:
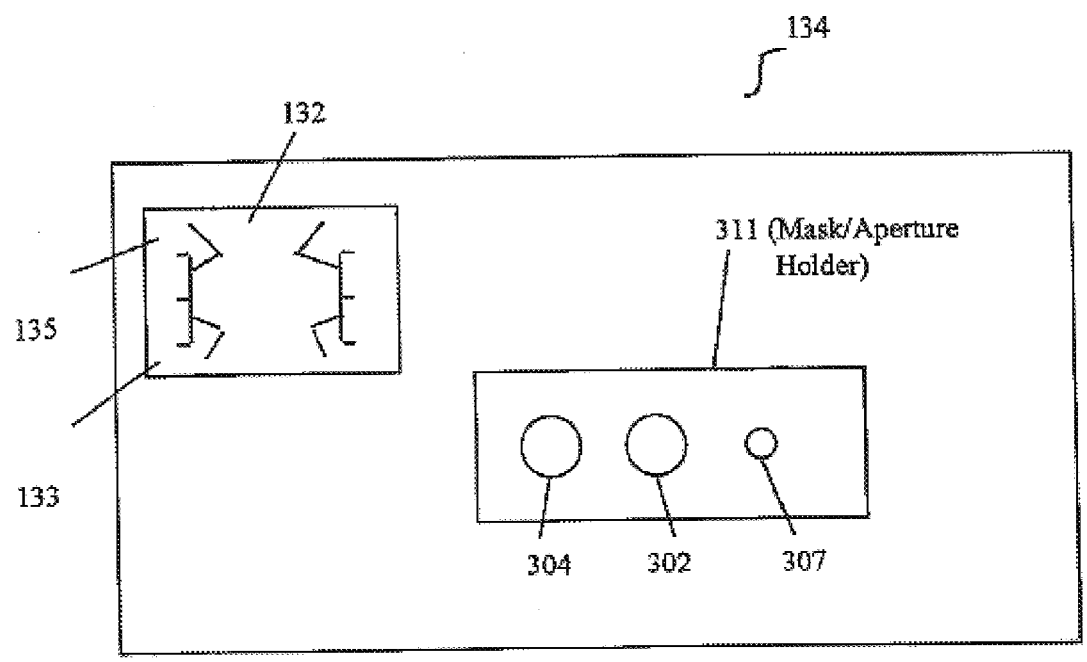
FIG. 4 is a front view line drawing of a device-readable enablement medium according to a preferred embodiment of the invention.

In order to control the enablement and use of the laser platform 102 for the delivery of a customized corrective instruction 120, a device-readable medium 134 as preferably illustrated in FIG. 4, is utilized. The medium 134 includes a data storage section 133 that is preprogrammed with a first corrective instruction reference 132. The first corrective instruction reference 132 will match an encryption code 120' corresponding to a customized corrective instruction 120 generated by the calculation module 150 based upon the input data 151. The laser platform 102 is equipped with a device-readable medium reader 130 which acts in one capacity as a lock and key mechanism, so to speak. Thus, when the readable medium 134 is inserted into and read by the reader 130, a necessary condition enabling the laser platform 102 to execute the customized corrective instruction 120 will be a recognition of the first corrective instruction reference 132 corresponding to the encoded customized corrective instruction 120'. This recognition is preferably accomplished in a configuration file 119 operably associated with, and preferably located in, the laser platform 102. A graphical user interface 144 is operably associated with the laser platform 102 and the configuration file 119 to further enable execution of the customized corrective instruction 120, as will be discussed in greater detail below.

Figure 3:
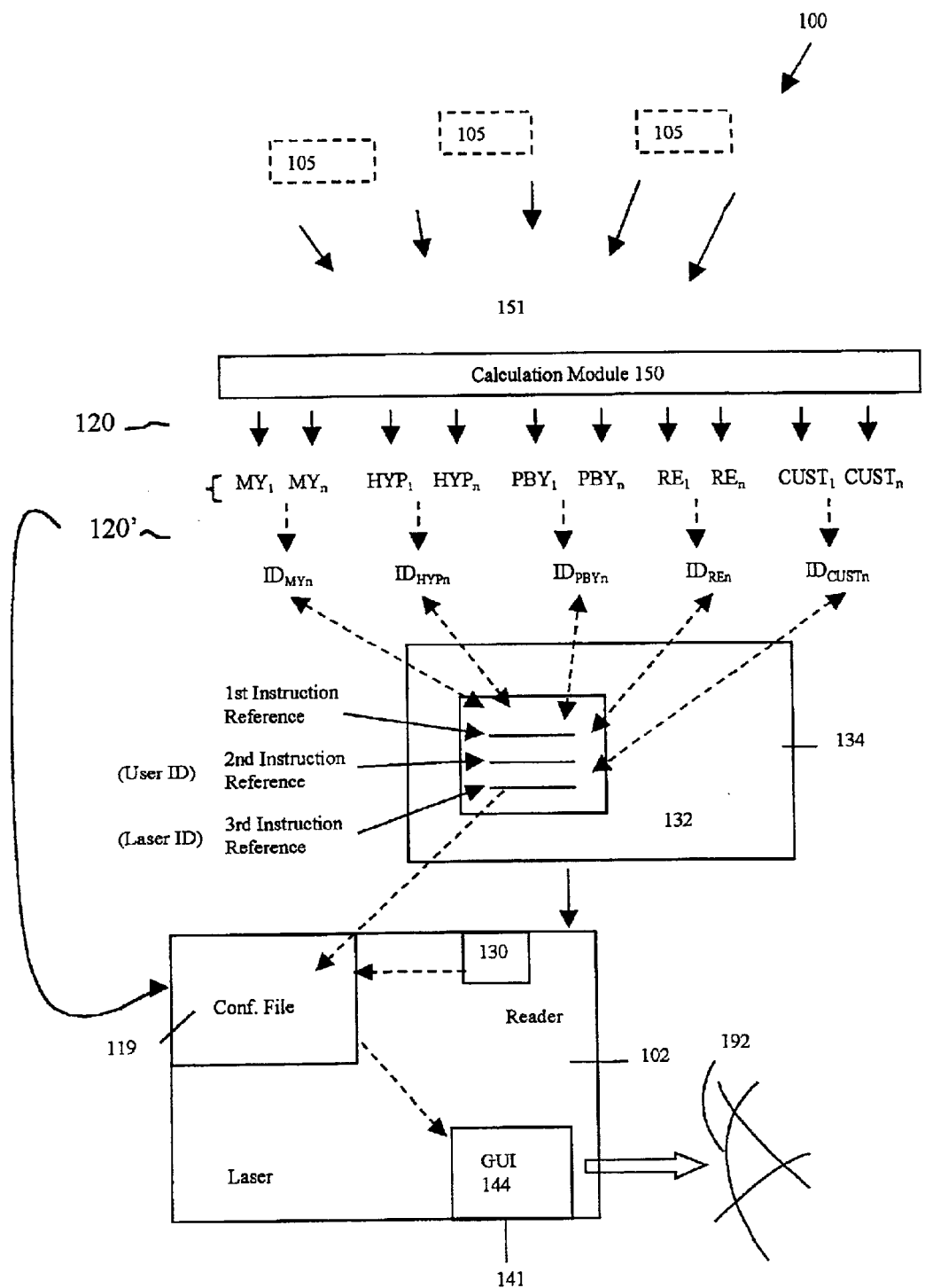
FIG. 3 is a block diagram of a more detailed illustration of the system of FIG. 2.

A further illustration of a preferred embodiment of the laser vision correction system 100 is illustrated in FIG. 3 and is described as follows. Ultimately, a laser vision correction treatment 190 in the form of a programmed series of ablating laser pulses will be directed to a patient's eye 192 to reshape the cornea in an attempt to correct a refractive defect of the patient's eye. Laser vision corrective surgery is typically provided, or being developed for, myopia, hyperopia, presbyopia, retreatment, customized treatment, and other conditions, as appreciated by those skilled in the art. The determination of a particular refractive defect starts with diagnostic information about the patient's eye and its visual quality. This diagnostic input data 151 can be generated by one or more diagnostic devices including wavefront sensors, topography devices, ultrasonic pachymeters, optical coherence tomography (OCT) devices, refractometers, slit lamp ophthalmoscopes (SLOs), iris pattern recognition apparatus, and others, well appreciated by those skilled in the art, and by other pertinent information that may be supplied by the practitioner including surgical environmental conditions, particular patient data, surgeon factors, and others. As used herein, the diagnostic platform 105, not a part of the invention per se, is used to collectively refer to any or all of the appropriate means for providing diagnostic information indicative of the patient's refractive defect. The appropriate input data 151 is fed to a calculation module 150. Preferably, the calculation module 150 comprises software that uses the input data 151 to determine one or more of an appropriate myopia treatment ($MY_n$), hyperopia treatment ($HYP_n$), presbyopia treatment ($PBY_n$), etc., 120 as shown. As an illustrative example, a Zywave® wavefront sensor (Bausch & Lomb Incorporated, Rochester, N.Y.) includes a computer that runs software known in the industry as Zylink® ablation computation software. Zylink uses the wavefront diagnostic data to determine an appropriate shot file for execution by a laser platform such as a Technolas 217Z® laser. Despite the fact that most ablation algorithms are determined by the laser manufacturers, surgeons constantly develop personalized nomograms based upon relevant outcome influencing factors which they have determined optimize their treatment outcomes. For example, a surgeon in Hong Kong may modify the calculated treatment to the extent permitted with a customized nomogram that produces optimized myopic correction for Asian patients. Similarly, for example, a surgeon in Florida may obtain optimized surgical outcomes using a different myopia treatment nomogram that compensates for humidity effects on outcome. Thus the calculation module 150 may calculate one myopia treatment ($MY_1$,) based upon a particular set of input data, and a different customized myopia treatment ($MY_2$) based upon a different set of input data. Likewise, one or more hyperopia treatments, presbyopic treatments, retreatments, customized treatments, or other treatments can be determined by the calculation module. These are listed as $HYP_1$, $HYP_2$ ..., $MY_1$, $MY_2$ ..., $PBY_1$, $PBY_2$ ..., etc., in the FIG. 3. Each of these calculated treatments becomes a customized corrective instruction 120 that is executable by an enabled laser platform 102 upon appropriate command. Advantageously, via the invention, the laser platform 102 has become a "dumb black box," so to speak, because the instruction for execution by the laser platform has been calculated externally of the laser platform.

With further reference to FIG. 4, the device-readable medium 134 has a data storage section 133 in or on which is pre-programmed the first corrective instruction reference 132. The first corrective instruction reference 132 corresponds to one or more of the encoded customized corrective instructions 120' determined by the calculation module 150. The data storage section 133 of the card medium 134 preferably has a data storage capacity of 1000 bytes or less making the card medium a relatively simple and inexpensive component suitable for single or pre-set limited use. The laser platform 102 is equipped with a card reader 130. The laser platform 102 further includes a configuration file 119. The configuration file 119 is preferably a hardware file that is adapted to recognize the instruction reference 132 on the card medium 134 corresponding to the encoded customized correction instruction 120'. Recognition of the first instruction reference by the configuration file 119 is a necessary condition for enabling the laser platform 102 to execute the predetermined customized corrective instruction 120. In a simple illustration, the calculation module 150 will generate a single myopia ablation treatment 120 based upon particular input data 151. The user of the laser system will then need a card medium 134 that has a first instruction reference 132 stored therein which corresponds to the code 120' associated with the customized corrective instruction 120. Use of the card medium in the laser platform and recognition of the corresponding instruction reference by the configuration file will unlock the laser platform for use and will enable the laser platform to carry out the particular customized corrective instruction 120.

Laser corrective surgery typically requires specific input from the surgeon; for example, the size of the optical zone (OZ) which is related to the depth of ablation for a particular treatment and further which is a determining factor as to whether a particular treatment can safely be carried out. This type of information is usually input into the system by the surgeon via a keypad 141 and a graphical user interface (GUI) 144 associated with the laser platform 102. According to a preferred aspect of the invention, the configuration file 119, upon recognition of a first corrective instruction reference 132 corresponding to an encoded customized corrective instruction 120', will call up an appropriate graphical user interface 144 which will allow the surgeon to input or confirm any deterministic data for the treatment. Thus, a customized corrective instruction for a myopia treatment may generate a different graphical user interface screen than a customized corrective instruction for a hyperopia treatment, and so on. In any event, it is a necessary condition for operation of the laser platform that the first instruction reference 132 match the customized corrective instruction code 120'. Preferably, at least one second instruction reference 123 stored in the card medium 134 will match a second code 123' and this will be a necessary and sufficient condition for enabling the laser platform 102 to execute the instruction 120. For example, the second instruction reference 123 may necessarily have to match a user ID code along with the matching first instruction reference 132 in order to unlock and enable the laser platform. More preferably, a third instruction reference 125 stored in the card medium 134 must necessarily match a laser platform ID such that only all three matching instruction references 132, 123, 125 are necessary and sufficient conditions for enabling the laser platform. In this manner, only an identified user may use an identified laser platform to carry out a particular customized corrective instruction. Other second, third, and/ or more instruction references may be stored in the card medium. For example, an instruction reference may correspond to an iris pattern code, or to an encoded LASIK flap thickness measurement. In the latter case, for example, a microkeratome platform may be adapted to accept the card medium and write to the storage section a lamellar code indicative of or relating to flap thickness. When the card medium is then engaged with the laser platform, recognition of a particular lamellar code may be a necessary condition for enabling the laser platform.

In another preferred aspect of the invention as shown in FIG. 4, the card medium 134 will be equipped with a laser platform disablement feature 135. The disablement feature 135 can be an electronic circuit or other well-known means that can be configured in such a manner to preset the number of uses of the card medium to enable the laser platform. Preferably, each card medium 134 could be preset to disable the laser platform after each single use. Alternatively, the card medium 134 could be programmed for two uses per card in the form of a single use on each eye of the patient. A new card medium will be required for each use of the laser, thus setting up an annuity structure for the card provider.

Figure 6:
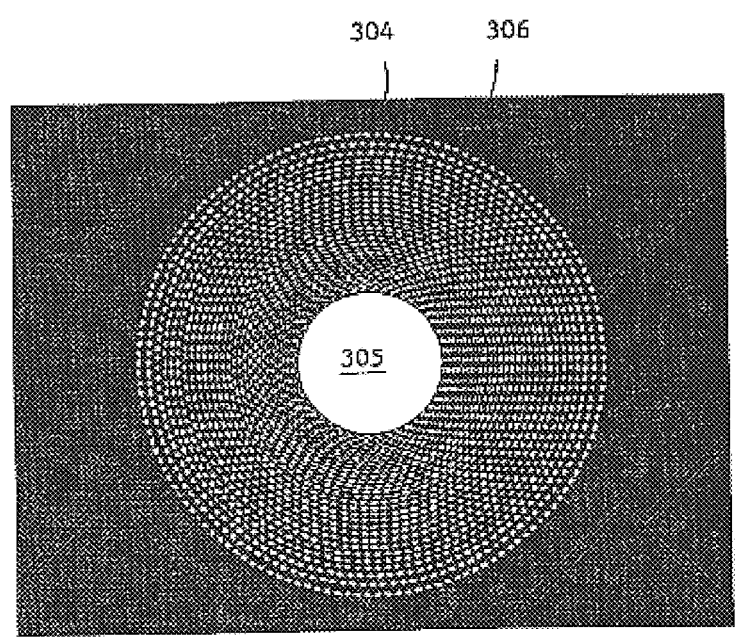
FIG. 6 is a more detailed illustration of the beam shaping feature of the enablement medium according to an embodiment of the invention.
Figure 8:
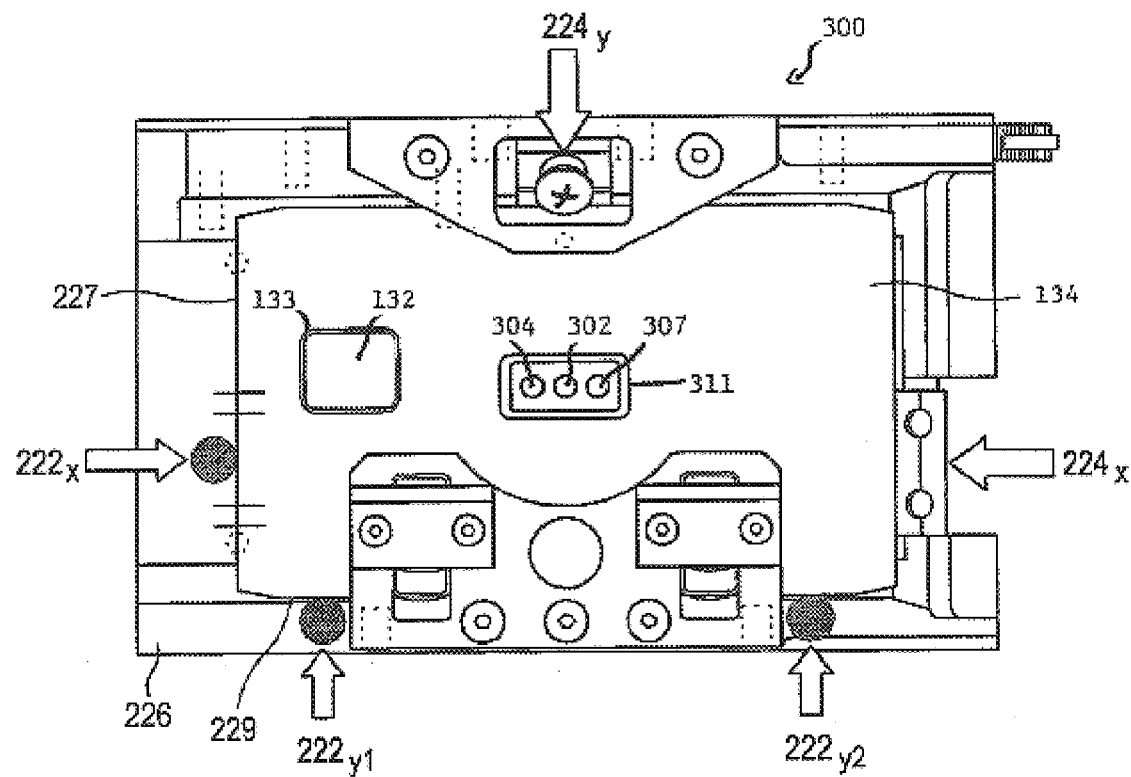
FIG. 8 is a front view illustration of an alignment and positioning apparatus for the enablement medium according to an embodiment of the invention.
Figure 5:
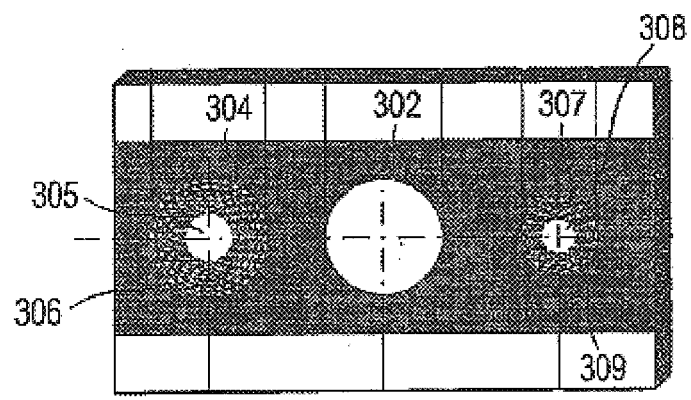
FIG. 5 is a drawing showing a beam shaping feature of the enablement medium according to a preferred embodiment of the invention.
Figure 7:
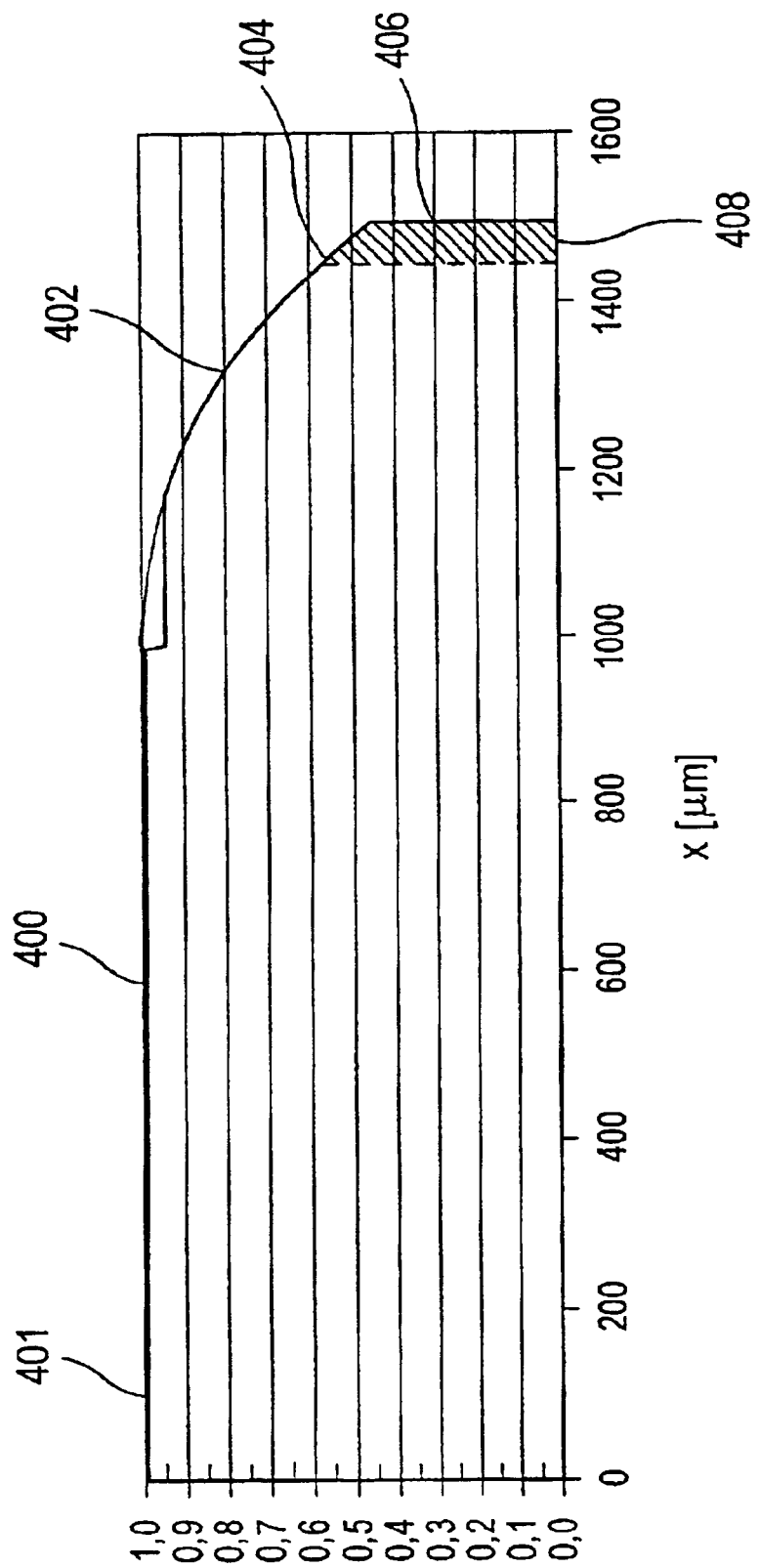
FIG. 7 is a graphical illustration of a laser beam intensity profile produced by the beam shaping feature of the enablement medium according to an embodiment of the invention.

With further reference to FIG. 4, another preferred aspect of the invention shows the card medium 134 with one or more apertures 304, 302, 307, in an aperture mask 311. Each aperture shapes and/or characterizes the laser beam passing through the aperture on its way to the target surface. In a preferred aspect illustrated with reference to FIG. 6, one of the apertures 304, referred to herein as a "soft-spot" aperture, has a central, directly transmitting aperture portion 305 surrounded by a plurality of smaller, diffracting apertures 306. The directly transmitting portion 305 of the aperture 304 essentially determines a beam spot diameter, while the diffractively transmitting portion 306 generates a particular beam energy profile which, in an exemplary case, is a soft-spot profile. FIG. 7 illustrates a soft-spot profile 400 which has the form of a truncated Gaussian distribution. Preferably, the directly transmitting portion 305 of aperture 304 has a diameter of 3 mm for directly transmitting the laser beam upon proper alignment, producing a 2 mm beam diameter spot on the target surface. Another aperture 307 is also a soft-spot aperture, preferably having a directly transmitting portion diameter of about 1.5 mm and delivering a 1 mm beam on target. Aperture 302 contains only a directly transmitting portion used for beam fluence calibration. Thus, the card medium 134 preferably has two soft-spot apertures 304, 307 of different overall diameters, and a hard spot aperture 302, as shown in FIG. 5. Upon proper alignment and positioning of the card medium 134 in the laser beam path of the module 102, two different beam spot sizes can selectively be projected onto the exposed cornea surface. Preferably, the two spot sizes on the corneal surface will be 2 mm and 1 mm. An automatic, pressure based mechanism 300, as illustrated in FIG. 8, is used to position and align the card 134 in the laser beam path in the module 102. Fixation points $222_{x,y}$ and pressure points $224_{x,y}$ are used as follows: the fixation points $222_{x,y}$ comprise three hardened cylinder pins that are press fit with high accuracy into a card holder 226. The card 134 is pushed into the holder 226 from right to left (as viewed in FIG. 7) until the left edge 227 of the card touches fixation point $222_x$ and the bottom edge 229 of the card touches fixation points $222_{y1}$ and $222_{y2}$. The card is fixated against the fixation points by pressure points $224_x$, $224_y$ which, preferably, are springs. By manufacturing the card 134 with high precision such that the exact location of the apertures are known, and the fixation points engage the card edges at the same locations, repeated positioning of the cards has shown a measured accuracy of ±5 µm or better. The interested reader is further referred to U.S. Pat. Nos. 6,090,100; 5,683,379; 5,827,264; 5,891,132, all of which are herein incorporated by reference in their entirety to the extent allowed by applicable laws and rules.

Referring again to FIG. 7, a preferable truncated Gaussian ablation profile (or spatial intensity distribution) 400 passed by the 3 mm soft-spot aperture 304, is shown. In the figure, the profile is normalized and only one-half the profile 400 is illustrated, solely for simplicity of the drawing, it being understood that the full profile 400 would be as if mirrored about the ordinate axis of FIG. 7. The 1 mm aperture 307 would pass a similar, but narrower, profile. As can be seen, a center portion 401 of the aperture profile 400 is flat or substantially flat, whereas an edge 402 of the profile 400 is continuous with the portion 401 and is rounded. The portion 401 is preferably symmetric about the radius of the profile and extends across about 60–80%, and, more preferably, across about 65–70% of the profile 400. At a certain point, such as an intensity threshold point 404 at which the eye tissue ablation intensity threshold is no longer reached, the profile 400 preferably quickly drops off or diminishes as a substantially square, vertical, or truncated edge 406. The ablation threshold and any variations in it are known in the art. The amount of energy falling below the threshold for ablation is preferably about 5% or less of the total energy encompassed by the profile 400.

The apparatus embodiments described herein naturally support method embodiments according to the invention. A preferred embodiment is a method for controlling a laser vision correction system that involves providing, to a third party, a device-readable medium (134) as set forth hereinabove, for use in a laser platform (102) to enable and execute a particular customized corrective instruction. Since provision of the card medium forms the basis of an annuity model for the card medium provider (typically the laser manufacturer), a single or preset use limitation (135) enabled by the card medium (134) promotes business transaction between the card supplier and the laser user. This is commonly referred to as the "per-procedure" model. In an aspect of this embodiment, the remunerative structure may be set according to the type and/or number of customized corrective instructions corresponding to the first instruction reference supplied on a particular card medium. For example, a physician may plan to perform 1,000 myopia laser procedures within a general patient base, and 100 customized myopia procedures within a select patient base. Based upon the input data, the calculation module may generate two different myopia treatment algorithms associated, respectively, with a non-customized myopia treatment and a customized myopia treatment. Accordingly, a user may purchase 1,000 cards containing a first matching instruction reference that will enable the laser platform to execute only a non-customized myopia treatment at some nominal cost per card unit. Similarly, the user may purchase 100 cards, each of which has a first matching instruction reference that will be recognized to enable the laser platform to execute a customized myopia treatment. These cards will have a different cost per card unit than the non-customized enabling cards. Thus, the remunerative basis of the card transaction can be structured upon the type of treatment, number of treatments, or other factors enabled by the particular code or codes stored on the card medium.

A related embodiment describes a method for controlling a laser vision correction system that involves generating a customized corrective instruction for correcting an ophthalmic refractive defect based upon diagnostic information indicative of that refractive defect; encoding the customized corrective instruction; providing a transferable, device-readable medium having a storage structure that contains a first corrective instruction reference that corresponds to the encoded customized corrective instruction; and providing, in a laser platform that is adapted to receive the device-readable medium, a means for recognizing the first instruction reference as a necessary condition for enablement and execution of the customized corrective instruction. In a preferred aspect, the recognition means includes a configuration file in the laser platform that upon recognition of the first instruction reference and, optionally, a second and/or third matching instruction reference which correspond to a user ID and/or a laser platform ID, for example, calls up a particular graphical user interface for additional data input by the surgeon. Upon appropriate input, the apparatus described hereinabove will, for example, position the card medium in the laser beam path and deliver a series of desired laser beam pulses to the patient's cornea to effect the desired treatment for correcting or at least improving upon the patient's refractive defect.

Based upon the foregoing, it can be appreciated that the card medium 134 including the first instruction reference 132 has greatly enhanced the flexibility of the vision correction system on several fronts over the prior art technology. Whereas, traditionally, a single enablement-type card was required for each procedure at a set fee per card unit, according to the invention a variety of pre-programmed enablement/instruction cards priced according to card/system enablement features are made available for use in a simplified laser platform.

Notwithstanding the preferred embodiments specifically illustrated and described herein, it will be appreciated that various modifications and variations of the instant invention are possible in light of the description set forth above and the appended claims, without departing from the spirit and scope of the invention.

We claim:

1. A device readable medium including a storage structure, for use in controlling a laser vision correction system, and having stored in said storage structure at least a first, readable, corrective instruction reference having a pre-programmed correspondence to an encoded corrective instruction.

2. A method for controlling a laser vision correction system, comprising: providing, to a third party, a device readable medium as set forth in claim 1, for use in a laser platform to en able and execute the laser vision correction.

3. The method of claim 2, wherein providing the device readable medium comprises providing the medium on a remunerative basis that is commensurate with a corrective instruction reference corresponding to a type and/or a number of customized corrective instructions.

4. The device readable medium of claim 1, further comprising disablement means for limiting the enablement of the laser platform to a pre-set number of uses.

5. The device readable medium of claim 4, wherein the pre-set number of uses is a single use.

6. The device readable medium of claim 4, wherein the pre-set number of uses consists of two uses limited to a single use for each of two eyes of a single patient.

7. The device readable medium of claim 1, further comprising a beam transmitting and characterizing feature.

8. The device readable medium of claim 7, wherein the beam transmitting and characterizing feature comprises an aperture.

9. The device readable medium of claim 8, wherein the aperture comprises a directly transmitting portion for sizing the beam and a diffractively transmitting portion for shaping an energy profile of the beam.

10. The device readable medium of claim 9, wherein the beam energy profile is a truncated Gaussian.

11. The device readable medium of claim 9, comprising two apertures having differently sized directly transmitting portions.

12. The device readable medium of claim 11, further comprising a third aperture having only a directly transmitting portion.

13. The device readable medium of claim 1, further wherein said first corrective instruction reference is a necessary but not a sufficient component for enabling a laser platform to execute a customized corrective instruction.

14. The device readable medium of claim 13, further comprising a second, readable corrective instruction reference stored in said storage structure, wherein said second corrective instruction reference is a necessary but not a sufficient component for enabling the laser platform to execute the customized corrective instruction.

15. The device readable medium of claim 14, wherein the first corrective instruction reference and the second corrective instruction reference are, in combination, sufficient components for the execution of the customized corrective instruction by the laser platform.

16. The device readable medium of claim 14, wherein the first corrective instruction reference and the second corrective instruction reference have, in combination, a data storage requirement $\leq 1000$ bytes.

17. The device readable medium of claim 14, wherein the second corrective instruction reference has a pre-programed correspondence to at least one of an encoded user ID and an encoded laser platform ID.

18. The device readable medium of claim 14, further comprising a third, readable, corrective instruction reference stored in said storage structure, wherein said third corrective instruction reference is a necessary but not sufficient component for enabling the laser platform to execute the customized corrective instruction.

19. The device readable medium of claim 18, wherein the first corrective instruction reference, the second corrective instruction reference, and the third corrective instruction reference are, in combination, sufficient components for the execution of the customized corrective instruction by the laser platform.

20. The device readable medium of claim 18, wherein the first corrective instruction reference, and the second corrective instruction reference, and the third corrective instruction reference have, in combination, a data storage requirement $\leq$1000 bytes.

21. The device readable medium of claim 18, wherein the third corrective instruction reference has a pre-programmed correspondence to at least one of an encoded user ID and an encoded laser platform ID.

22. A laser vision correction system, comprising:
   a calculation module adapted to receive an input data relating to a refractive defect of a patient's eye and to calculate a customized corrective instruction based upon said input data, said calculated customized corrective instruction being resident in said calculation module as an encoded customized corrective instruction corresponding to a pre-programmed first corrective instruction reference;
   a device readable medium including a storage structure having stored therein at least a first, readable, corrective instruction reference corresponding to the encoded customized corrective instruction; and
   a laser platform adapted to receive the medium and enabled to execute the customized corrective instruction upon a necessary recognition of the first corrective instruction reference corresponding to the encoded customized corrective instruction.

23. The system of claim 22, wherein the calculation module is external to the laser platform.

24. The system of claim 22, wherein the calculation module is a computer software routine running a laser ablation algorithm.

25. The system of claim 22, further comprising a graphical user interface (GUI) operably associated with the laser platform, and a configuration file operably associated with the laser platform and the GUI, wherein the configuration file will initiate a particular GUI associated with the customized corrective instruction only when the corresponding corrective instruction reference is recognized by the configuration file.

26. The system of claim 22, wherein the input data is indicative of a refractive defect of a patient's eye, and the customized corrective instruction comprises an ablation treatment instruction intended to remedy the refractive defect.

27. The system of claim 26, wherein the customized corrective instruction comprises a plurality of different customized corrective instructions defining a selection of laser vision correction treatments.

28. The system of claim 22, further comprising a diagnostic platform in operable communication with the calculation module, wherein said diagnostic platform is a source of the input data, and wherein the calculation module is a software routine resident in the diagnostic platform.

29. The system of claim 28, wherein the diagnostic platform comprises at least one of a topography device, a wavefront sensor device, an optical coherence tomography device, an ultrasound pachymetry device, an autorefractor device, a slit lamp ophthalmoscope device, and a subjective manifest refraction device.

30. The system of claim 22, wherein the medium has stored therein at least a second instruction reference that corresponds to a second encoded corrective instruction, wherein a recognition of the correspondence by the laser platform is a necessary and sufficient condition for enablement and execution of the customized corrective instruction.

31. The system of claim 30, wherein the calculation module resides in a diagnostic platform that generates at least some of the input data.

32. The system of claim 30, wherein the second encoded corrective instruction refers to at least one of a user ID and a laser platform ID.

33. The system of claim 30, wherein a total data storage requirement of all of the instruction references is $\leq$1000 bytes.

34. A method for controlling a laser vision correction system, comprising:
   determiing a customized corrective instruction for correcting an ophthlmic refractive defect;
   encoding said instruction;
   providing a pre-programmed first corrective instruction reference in a transferable medium that corresponds to said encoded instruction;
   providing, in a laser platform adapted for receiving said transferable medium, a means for recognizing the first instruction reference as a necessary condition for enablement and execution of the customized corrective instruction.

35. The method according to claim 34, wherein the recognition of the first instruction reference is a sufficient condition for enablement and execution of the corresponding customized corrective instruction.

36. The method according to claim 34, wherein determining the customized corrective instruction comprises using a diagnostic input data indicative of the ophthalmic refractive defect.

37. The method according to claim 34, wherein providing the pre-programmed first corrective instruction reference in the transferable medium comprises providing a device readable medium containing the instruction reference.

38. The method according to claim 34, further comprising:
   providing a GUI operably communicating with the laser platform, wherein said GUI is configured according to the first instruction reference and corresponding customized instruction.

39. The method according to claim 38, wherein providing the means for recognizing the first instruction reference comprises providing a configuration file in the laser platform that upon recognition of the instruction reference enables the GUI associated with the matching corrective instruction.

40. The method according to claim 34, further comprising:
   providing at least one of an encoded user ID and an encoded laser platform ID;
   providing at least a second corrective instruction reference in the transferable medium that corresponds to one of the encoded user ID and the encoded laser platform ID, wherein the at least second instruction reference is recognized in the laser platform as a necessary condition for enablement and execution of the corresponding customized corrective instruction.

41. The method according to claim 40, wherein the recognition of the first and second instruction references is a sufficient condition for enablement and execution of the corresponding customized corrective instruction.

42. The method according to claim 34, further comprising:
   providing an encoded user ID and an encoded laser platform ID; and
   providing a second corrective instruction reference and a third corrective instruction reference in the transferable medium which correspond to the encoded user ID and the encoded laser platform ID, wherein the second instruction reference and the third instruction reference are recognized in the laser platform as necessary conditions for enablement and execution of the customized corrective instruction.

43. The method according to claim 42, wherein the recognition of the first, second, and third instruction references is a sufficient condition for enablement and execution of the corresponding customized corrective instruction.

44. The method according to claim 34, further comprising providing, in the transferable medium, a disablement means for controlling the use of the laser platform.

45. The method according to claim 44, wherein the laser platform is controlled for a pre-set number of uses.

46. The method according to claim 45, wherein the pre-set number of uses is a single use.

47. The method according to claim 45, wherein the pre-set number of uses is a single use for each of two eyes of a patient.

* * * * *

UNITED STATES PATENT AND TRADEMARK OFFICE
CERTIFICATE OF CORRECTION

PATENT NO. : 6,814,729 B2
DATED : November 9, 2004
INVENTOR(S) : Gerhard Youssefi et al.

It is certified that error appears in the above-identified patent and that said Letters Patent is hereby corrected as shown below:

Column 9,
Line 64, insert -- customized -- after the word "encoded" and before the word "corrective"

Column 10,
Line 51, replace "≦" with -- less than or equal to --

Column 12,
Line 5, replace "≦" with -- less than or equal to --

Signed and Sealed this

Ninth Day of August, 2005

JON W. DUDAS
*Director of the United States Patent and Trademark Office*